(12) United States Patent
Wellens

(10) Patent No.: US 11,045,277 B2
(45) Date of Patent: Jun. 29, 2021

(54) PRE-CLEANING SYSTEM FOR FLEXIBLE ENDOSCOPES: BATH AND METHOD

(71) Applicant: Z-PROJECTS BVBA, Massenhoven (BE)

(72) Inventor: Serge Wellens, Massenhoven (BE)

(73) Assignee: Z-PROJECTS BVBA, Massenhoven (BE)

( * ) Notice: Subject to any disclaimer, the term of this patent is extended or adjusted under 35 U.S.C. 154(b) by 348 days.

(21) Appl. No.: 15/766,129

(22) PCT Filed: Oct. 6, 2016

(86) PCT No.: PCT/EP2016/073933
§ 371 (c)(1),
(2) Date: Apr. 5, 2018

(87) PCT Pub. No.: WO2017/060390
PCT Pub. Date: Apr. 13, 2017

(65) Prior Publication Data
US 2018/0296303 A1   Oct. 18, 2018

Related U.S. Application Data

(60) Provisional application No. 62/238,946, filed on Oct. 8, 2015.

(30) Foreign Application Priority Data

Oct. 7, 2015   (GB) ...................................... 1517735

(51) Int. Cl.
*A61L 2/18*   (2006.01)
*A61B 90/70*   (2016.01)
(Continued)

(52) U.S. Cl.
CPC ................ *A61B 90/70* (2016.02); *A61B 1/12* (2013.01); *A61B 1/122* (2013.01); *A61L 2/07* (2013.01);
(Continued)

(58) Field of Classification Search
None
See application file for complete search history.

(56) References Cited

U.S. PATENT DOCUMENTS 3,801,279 A   4/1974   Grieco
6,267,124 B1 *   7/2001   Bowden ................. B08B 3/041
134/111

(Continued)

FOREIGN PATENT DOCUMENTS

DE   29819904 U1   2/1999
DE   20217881 U1   2/2003
(Continued)

OTHER PUBLICATIONS

International Preliminary Report on Patentability in related Application No. PCT/EP2016/073933, dated Apr. 10, 2018.
(Continued)

*Primary Examiner* — Mikhail Kornakov
*Assistant Examiner* — Ryan L Coleman
(74) *Attorney, Agent, or Firm* — Bacon & Thomas, PLLC

(57) ABSTRACT

An apparatus and method for pre-cleaning or cleaning of objects such as medical, surgical and endoscope devices especially having lumens or channels are described of a sink for holding cleaning liquid. The PLC and software controls operators, doctors, patients and instruments through every step during the procedure which includes integrated leak test automatically, integrated channel rinsing, integrated camera, automatic brush control and endoscope layers with lift system.

20 Claims, 4 Drawing Sheets

(51) Int. Cl.
  *A61B 1/12* (2006.01)
  *A61L 2/07* (2006.01)
  *A61L 2/24* (2006.01)
  *A61L 2/26* (2006.01)

(52) U.S. Cl.
  CPC .............. *A61L 2/24* (2013.01); *A61L 2/26* (2013.01); *A61B 1/123* (2013.01); *A61B 1/125* (2013.01); *A61B 2090/701* (2016.02); *A61B 2090/702* (2016.02); *A61L 2202/14* (2013.01); *A61L 2202/15* (2013.01); *A61L 2202/17* (2013.01); *A61L 2202/24* (2013.01)

(56) References Cited

U.S. PATENT DOCUMENTS

2009/0044845 A1* 2/2009 Cui .................. A61B 1/123
  134/56 R
2010/0059515 A1* 3/2010 Wilkerson ......... A47G 19/2227
  220/260
2016/0249794 A1* 9/2016 Suzuki ................ C02F 1/001
  134/169 C
2016/0271659 A1* 9/2016 Russ ..................... A61L 2/10

FOREIGN PATENT DOCUMENTS

DE  202012002701 U1  5/2012
EP    2025282 A2    2/2009

OTHER PUBLICATIONS

International Search Report for PCT/EP2016/073933 dated Jan. 16, 2017 (5 pages).
Written Opinion for PCT/EP2016/073933 dated Jan. 16, 2017 (7 pages).

* cited by examiner

PRE-CLEANING SYSTEM FOR FLEXIBLE ENDOSCOPES: BATH AND METHOD

The present invention relates to methods and apparatus for cleaning, rinsing or pre-cleaning of objects especially reusable medical or surgical equipment, apparatus or devices, and also cleaning of such equipment or devices that are hollow such as tubular medical or surgical devices with lumens such as endoscopes.

BACKGROUND OF THE INVENTION

Prior art devices exist for effective pre-cleaning of medical and surgical devices. Safe reuse of medical devices such as flexible endoscopes depends upon the effectiveness of the pre-cleaning process. One method of handling in pre-cleaning uses manual leak tester, manual channel rinsing, brushing the channels with water, for example, having additives such as solvents, detergents or antibacterial and/or antiviral agents, enzymatic detergents. With manual pre-cleaning, there is no possibility to clean endoscopes based with a validated and reprocessed procedure. The first step in a cleaning process is usually to rinse off all blood, bodily fluids and tissue as soon as possible after use before manual or mechanical cleaning in an endoscope washer.

Pre-cleaning medical flexible endoscopes demands leakage test and hand operation using a syringe or brush and this can involve flushing the lumen of the device several times. Thus, changing from cleaning of handheld small endoscopy instruments to large devices with lumens involves a lot of manual activity. A typical sequence can be:

a) Clean the surface of the endoscope directly after use with a wipe,
b) Dry leakage test to control leakages after examination,
c) If no leaks detected, rinse the channels with water and product,
d) Brush with a suitable cleaning brush until all residues have been removed from the surface taking special care of products with hidden crevices, lumens or complex geometries,
e) After brushing, thoroughly rinse several times with a suitable cleaning solution with a syringe,
f) Rinse the product with water.

Every effort and cleaning step needs to be made to prevent anything remaining attached to the devices, even as small as bacteria or viruses. Due to the risk of coagulation the temperature of cleaning baths must be kept below a certain temperature, e.g. 30° C., and this means that there is no risk to create extra aerosols. On the other hand, introducing software to control each cleaning step can avoid mistakes.

At the end of the cleaning process the devices or instruments should not show any visual contamination and the total amount of residual proteins on and in the devices or instruments should be (EN ISO 15883-1:2006, C2) less than 100 μg (warning level) or 200 μg (threshold) or in some countries less than 6.4 μg/cm$^2$. Usually effective cleaning requires a sequence of cleaning processes, e.g. a series of tanks and/or washing machines. The overall safety and efficacy of the complete cleaning process can be improved if the early processes such as rinsing and pre-cleaning do a maximum to remove unwanted material usually called "soils".

SUMMARY OF THE INVENTION

It is an object of the present invention to provide a good pre-cleaning apparatus and method.

Advantages of the apparatus and method according to embodiments of the present invention can be one or more of the following:
  economical;
  solves one or more of the problems encountered with prior art apparatus such as, for example, the cleaning of reusable medical and/or surgical devices, in particular tubular items such as endoscopes;
  Automatic or manual controlling leakage test, channel rinsing, temperature of the cleaning liquid, brushing with camera control and rinsing;
  Automatic or manual imaging or video recordings and identification of sink used, and endoscope cleaned as well as operational parameters of the apparatus, e.g. temperature of cleaning liquid, control of blocked valves, during the pre-cleaning process;
  Procedure to maintain cleanliness by physical adjustments of the equipment to freeze operation until certain cleaning and maintenance procedures are carried out.
  Recycling of cleaning fluid
  Avoidance of the risk of cross-contamination.

One aspect the present invention is an apparatus for pre-cleaning objects such as flexible endoscopes or medical or surgical devices optionally having a lumen, the apparatus comprising:
one or two sinks for holding cleaning liquid, the sinks having at least a first and a second wall and a bottom and being adapted to hold cleaning liquid and to expose the cleaning liquid automatically to the objects;
a channel in the form of a depression in the bottom of the sink, and
a drain located in the channel for draining cleaning liquid from the sink.

In this aspect of the present invention an apparatus for pre-cleaning of objects such as medical or surgical devices especially having lumens and channels, is provided.

In another aspect of the present invention a console cleaning system can be provided that integrates a leakage control with a cleaning step, and one or two or more cleaning sinks. The sinks can have integrated draining layers with a lift system having an actuating mechanism, for example pneumatic cylinders or electric motors with rack and pinion to raise and lower the draining layers. Raising can brings the medical device to be cleaned out of the cleaning liquid to allow manual inspection and brushing and lowering brings the medical device to be cleaned into and under the cleaning liquid to rinse it.

Further an integrated image capture device such as a camera can be provided to be used in control and recoding of the brushing step.

In accordance with another aspect of the present invention such as systems is automated through the use of a PLC. The console can include a start button and a reset button to start or reset a predetermined sequence of leakage test, brushing, lowering and rinsing, raising and further brushing and so on.

An inlet can be provided for delivering cleaning liquid for the cleaning of objects with a lumen or flexible endoscopes. A bottom skimmer can be provided for moving sunken debris or detritus along the bottom of the sink towards and down the drain. This bottom skimmer can be adapted to insert cleaning liquid through a wall of the sink for moving sunken debris or detritus towards and down the drain. The insertion of the cleaning liquid is preferably through a wall of the sink remote from the drain and is preferably at a lower level than the inlet for cleaning liquid. The bottom skimmer can comprise a line of spray nozzles located in the wall for inserting liquid through the wall.

The present invention also provides a control system for a console cleaning system comprising a main controller to control the operation of the following optional control elements:

- A source 4 of water supply and for optional connection to a chemical dispensing system for dispensing cleaning reagents into the cleaning liquid e.g. water;
- A drain 1 with a controllable valve such as a solenoid valve system 21;
- An overflow drain 8 to control the level of water in the sink;
- A recycling filter 41 to filter cleaning fluid taken from a sink 10 through the drain 1 filtered cleaning liquid being returned to the or a pre-cleaning sink;
- Compliance recording equipment such an image capture device such as one or more cameras 3 to be used during checking and recording of one or more steps such as of a brushing step;
- Further compliance recording equipment such as an electronic identification system for identifying which sink is used for pre-cleaning and which medical device such as an endoscope is cleaned, e.g. using a barcode scanner of a barcode on an endoscope or on a sink, or using an RFID tag identification wireless system to identify and record details of an RFID tag on a sink and on an endoscope.
- Vertically movable one or more actuators such as a number, e.g. three hydraulic cylinders or one pneumatic cylinder 7 or one or more linear motors or rack and pinion stepper motors for a lift system 2 of a draining layer 25. The one or more pistons 7 of the cylinders or one or more linear motors or rack and pinion stepper motors extend and lift the draining layer 25, optionally the draining layer 25 is lifted by the lift system 2 and rotated through an angle such as 30 to 90° into an inclined or vertical position. Once lifted the draining layer can be prevented from being lowered until cleaning operations have been carried out to provide further compliance recording equipment;
- Optional one or more sensors such as one or more pressure and/or flow sensors on any some or each drain, liquid inlet, or nozzle to detect if any of these drains, inlets, inlets or nozzles are blocked;
- A number such as four spray nozzles 5 to be used as a bottom skimmer and to rinse the bottom of the sink;
- A water inlet 4;
- An integrated indicator strip 6 such as a coloured LED strip on a side of the sink for indicating the status of an approval process;
- A display 9 such as a curved LED, LCD or plasma monitor which can be a touch screen and can be used not only to display the status of the cleaning process but also to control it through commends linked to visible icons;
- A data input device 12 such as a glass keyboard which is preferably waterproof with a touchpad;
- A microcontroller or computer for automatically progressing through a cleaning sequence after pushing of a start button;
- A channel flushing connection 11 to which any suitable pipe, tube or conduit can be connected to use for flushing with cleaning liquid and/or air and/or steam;
- Leak test connection 22 to which any suitable pipe, tube or conduit can be connected to use for leak testing e.g. with air or liquid or vacuum;
- Reset button 13;
- Start Button 14;
- Endoscope draining layers 25 supported on the lift system 2, the draining layers having openings such as slits to allow cleaning liquid to drain through when the lift system lifts the medical device to be cleaned upwards and out of the cleaning liquid. The lift system provides three positions for a draining layer 25, a lowered position where the medical device such as the endoscope is below the level of the cleaning liquid, a first raised position when the medical device such as the endoscope is above the level of the cleaning liquid, and a further raised position when the draining layer is raised still further and rotated.
- Furniture such as a console 20 for housing the sinks 10.

Embodiments of the present invention will now be described with reference to the following drawings.

BRIEF DESCRIPTION OF THE DRAWINGS

Reference numbers in one figure refer to the same functional object with the same reference number in another figure unless defined differently.

DETAILED DESCRIPTION OF THE INVENTION

Figure 1:
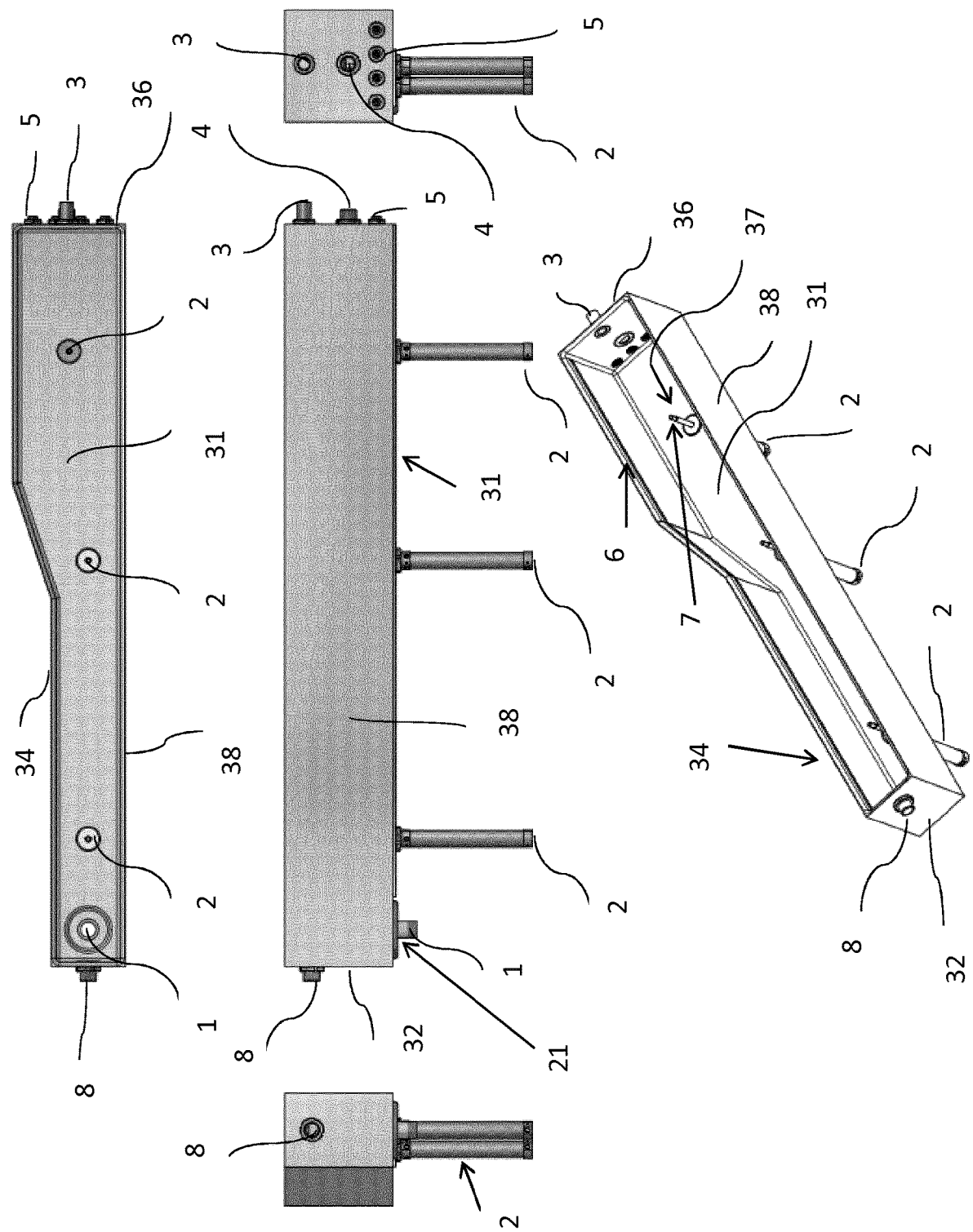
FIG. 1 is a top view, side view, end view and bottom view of the endoscope cleaning sink according to an embodiment of the present invention.

The present invention will be described with respect to particular embodiments and with reference to certain drawings but the invention is not limited thereto but only by the claims. The drawings described are only schematic and are non-limiting. In the drawings, the size of some of the elements may be exaggerated and not drawn on scale for illustrative purposes. The dimensions and the relative dimensions do not correspond to actual reductions to practice of the invention.

Figure 2:
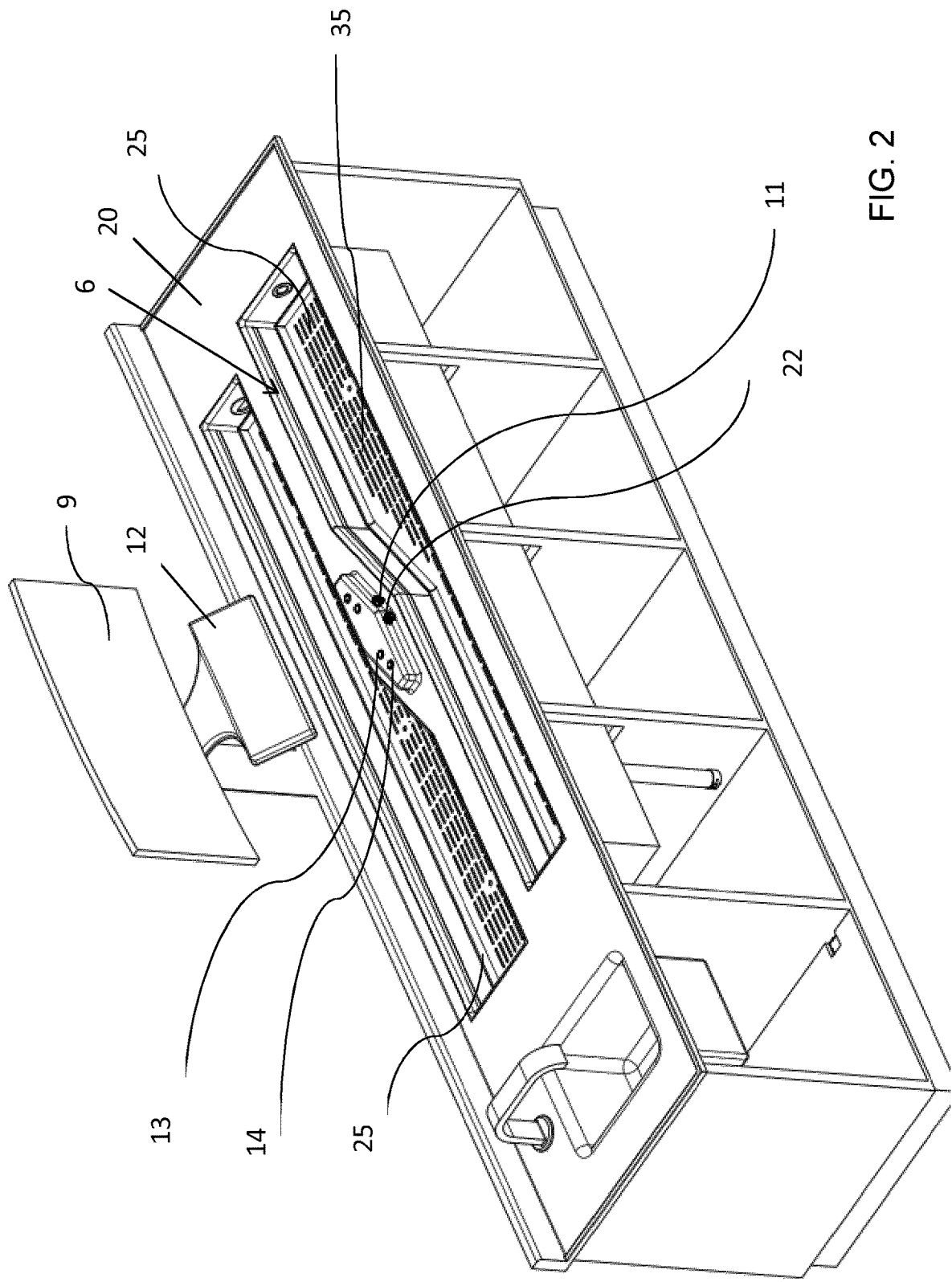
FIG. 2 shows an endoscope pre-cleaning apparatus according to an embodiment of the present invention. The pre-cleaning apparatus can be configured with one or two sinks.

As shown schematically in FIGS. 1 and 2, a bath, tub, basin or sink 10 of an embodiment of the present invention includes walls 32, 34, 36, 38, and a draining layer 25 and a bottom 31 defining a volume 35 for holding a liquid for pre-cleaning or cleaning of contaminated objects such as used endoscopes and/or surgical devices. In the description and claims the term "sink" will be understood to include any of a bath, tub, basin or tank. The form and size of the sink 10 can be chosen based on the size and shape of the objects to be cleaned. Most of these objects can have an open or several hollow part such as a lumen and channels. The preferred liquid used for cleaning is water with or without other chemicals. Other aqueous solutions that can be used can include enzymatic solutions or solutions including detergents, soaps, antiseptics, disinfectants, silver based ionic species, etc. In some cleaning processes other liquids can be used such as isopropyl alcohol, ethanol, acetone or mixtures of these or any other suitable solvent cleaning chemicals can be used as the cleaning liquid. The sink 10 is preferably held in a frame or console 20 preferably at an ergonomic working height. The sink 10 is adapted to carry out one or more cleaning procedures, e.g. leak testing, soaking, scrubbing, brushing, rinsing, pre-cleaning. Preferably brushing is especially used because of the bioburden, debris or detritus which are difficult to clean simply by rinsing or spraying and, hence, need brushing. The draining layer 25 is arranged to be movable in the vertical direction to bring objects to be cleaned out of the cleaning liquid for visual inspection and for manual operations such as brushing and to lower them into the cleaning liquid for rinsing. The draining layer 25 can also be arranged to be movable in the vertical direction under the action of the lifting system followed by rotation though and angle such as 30° to 90° so that the draining layer 25 is inclined to the vertical or is vertical. The draining layer 25 has holes such as slits to allow cleaning liquid to drain through.

The sink 10 has walls (e.g. four 32, 34, 36, 38) extending upwardly from the bottom 31 of the sink 10 to enclose a volume 35. The walls (e.g. 32, 34, 36, 38) can be flat but also curved walls could be used, e.g. forming a circular, elliptical or oval shape in horizontal cross-section. For example an elliptical tank has two half-elliptical walls and a bottom. The sink 10 should have at least two walls facing each other and enclosing a volume. For example, the sink 10 can have four side walls 32, 34, 36, 38 forming a convenient shape such as the shape of an endoscope. Other shapes may be suitable depending upon the application.

The walls 32, 34, 36, 38 and bottom 31 should be smooth and should have no blind spots or places where eddies can form. The material from which the walls 32, 34, 36, 38, draining layer 25 and bottom 31 are made should not support attached cell growth, e.g. of human cells, bacteria, algae, amoebas, microorganisms, plants, or other biological materials. Suitable properties for the material of the sink 10 are strength and rigidity, chemical and temperature resistance, good impact, abrasion, cracking and shatter resistance, surface hardness, and chemical inertness. The bottom 31 can be horizontal, i.e. is flat and horizontal or may slope downwards towards the drain 1. The drain 1 may include a controllable valve 21 such as a solenoid valve and can be under control of a controller such as a PLC. A recycling filter 41 can be provided to filter cleaning fluid taken from a sink 10 through the drain 1, the filtered cleaning liquid being returned to the or a pre-cleaning sink 10.

The material of the walls 32, 34, 36, 38, draining layer 25 or bottom 31 should also not initiate coagulation of proteins. For medical devices the sink 10 should be operated at a temperature of less than 60° C., less than 45° C. and preferably in the range of 30 to 40° C. to avoid coagulation of proteins.

A preferred material for the sink 10 is stainless steel. Alternatively, another appropriate metal could be selected for the material of the body of the sink 10. If the sink 10 is made as a replaceable insert then other materials, such as plastic, can be suitable. Such a material can be a synthetic resin. The sink 10 can be made by any suitable method such as machining, fabrication and welding, or moulding from a plastic material. Low surface energy non-polar plastics are preferred such as polypropylene or polyethylene.

The upper edges of the sink 10 are preferably continuous, smooth and rounded so that there is no risk of injury to operators. The upper edges can be designed as flanges such that if the sink 10 is constructed as an insert, then the insert can hang from these edges, e.g. in a console 20.

The sink 10 preferably has one or more overflows or weirs such as an overflow 8 that allows overflow of the liquid from the main body of the sink 10, thus defining the upper level of the liquid in the sink 10. If one or more weirs are used (not shown) these may be spaced from a wall of the sink 10 to form thereby a second channel with the rest of the sink forming a first channel. On the side of the one or more weirs which is remote from the main body of the sink 10, one or more drains can be provided which communicate with the first channel to drain liquid from the first channel. The sink 10 is preferably adapted to make liquid flow over the weir, from an inlet 4 to the one or more drains. Where no weir is used the sink 10 may have a single volume and a drain 1 in the bottom 31 and an overflow 8 (as shown).

To push non-floating debris and detritus towards bottom drain 1 a bottom skimmer 37 is provided. This skimmer 37 can be a plurality of holes or slits or nozzles 5 which are provided in a wall 36 of the sink 10, e.g. in a line of nozzles 5, in the wall 36 opposite to the wall 32 close to which the drain 1 is located. Liquid and/or gas can be pumped from a conduit into the sink 10 through the holes or nozzles 5 to drive non-floating debris and detritus towards the drain 1. Optionally, an upper skimmer can be provided (not shown) that pushes floating debris and detritus towards the overflow 8 or over the weir if provided and, hence, out of the sink 10, e.g. to the one or more drains. The upper skimmer preferably extends for the complete length of the wall opposite the weir so that the flow of liquid out of the holes or nozzles does not generate eddies where material can become trapped, but rather produces a uniform movement across the body of the sink. The bottom skimmer 37 should be arranged such that it does not generate eddies where material can become trapped but rather produces a uniform movement across the body of the sink 10.

Pumps and level sensors are provided (not shown) to regulate the level of the liquid in the sink 10. The flow through the one or more drains 1 may be due to gravity, or suction may be applied to the drain 1 to suck out liquid, debris and detritus. In addition or alternatively, a barrier plate or swimmer (not shown) may be physically moved across the top of the liquid in the sink 10, e.g. by means of hydraulic rams to push the detritus or debris towards and over the weir and, hence, to the one or more drains. A plate whether solid or porous in the form of a mesh is however less preferred in comparison to the holes or nozzles, as a plate may be more difficult to keep clean.

The sink 10 is provided with leak tester connection 22. This connection allows fixing of any suitable pipe, conduit or tube for leakage testing of the medical device to be cleaned such as an endoscope. Liquid or fluid pressure may be applied through this connection or vacuum. Also pressure may be measured through this connection to indicate the presence of leaks. Also a channel flush connection 11 is provided which can be used with sufficient electrical supplies, pumps, conduits, heaters and valves and access to drains to allow continuous, pulsating or intermittent flow of liquid into and through the sink 10 for cleaning the endoscopes or other medical devices. For example the connection 11 may be used with a flushing outlet such as a nozzle, liquid supply and a pump for jetting or spraying liquid and/or solvents and/or steam optionally at high pressure through the outlet to flush hollow spaces such as a lumen of a medical or surgical device or an endoscope. This cleaning is preferably done by hand as the control of the cleaning process can then be extended or modified by human intervention and recorded with an image capture device such as a camera 3. The jetting can be continuous, pulsating or intermittent. The connection 11 and the flushing outlet may include a nozzle and/or may include a tube extension or a flexible tube extension (not shown) that allows the jetted liquid, air or steam to be directed into a lumen of a medical or surgical device or endoscope. The end of any such tube or outlet may be fitted with a means for attachment to the lumen of the medical or surgical device or endoscope to be cleaned. Such means can be an adaptor which can be constructed for sealed attachment both to the outlet or outlet tube as well as to the lumen. The connection may be extended for use as a connection to spray pistols and/or overhead sprays for manual cleaning.

A control unit (not shown) is provided which can be programmed to operate the pumps and valves in a manner suitable to control the cleaning process. Such a controller may be a PLC which has been suitably programmed. Compliance recording equipment such an image capture device such as one or more cameras 3 can be used for checking and recording of one or more steps such as of a brushing step. Further compliance recording equipment can be provided such as an electronic identification system for identifying which sink is used for pre-cleaning and which medical device such as an endoscope is cleaned, e.g. using a barcode scanner of a barcode on an endoscope or on a sink, or using an RFID tag identification wireless system to identify and record details of an RFID tag on a sink and on an endoscope. Each step can be controlled through a bar code scanner or RFID, which means that nurse, doctor, patient, instrument and operator are traced during the pre-cleaning procedure and the cleaning process recorded by means of camera 3. The status of the cleaning can be displayed on a display 9 which can be any suitable display such as a touchscreen or can have a separate keyboard or touchscreen 12. The touchscreen 9 or 12 can be used to control the cleaning process by activating commands by touching the screen. The display 9 can be for example any fixed format display such as an LED, LCD or plasma display. The controller can be adapted to record all steps of the cleaning including capturing images from the image capture device 3.

Figure 3:
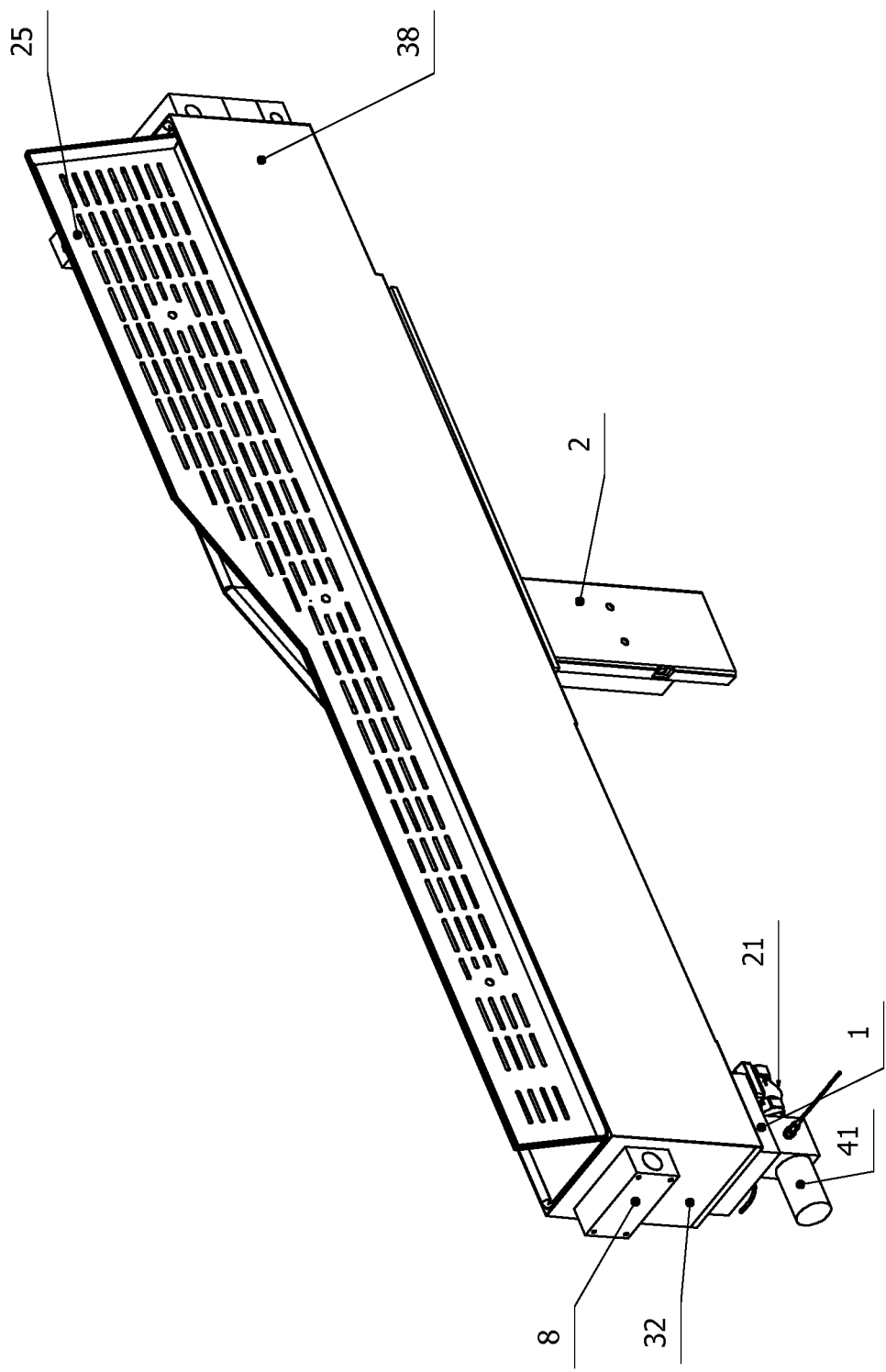
FIGS. 3 and 4 show an endoscope pre-cleaning apparatus and a detail of an endoscope pre-cleaning apparatus according to embodiments of the present invention.
Figure 4:
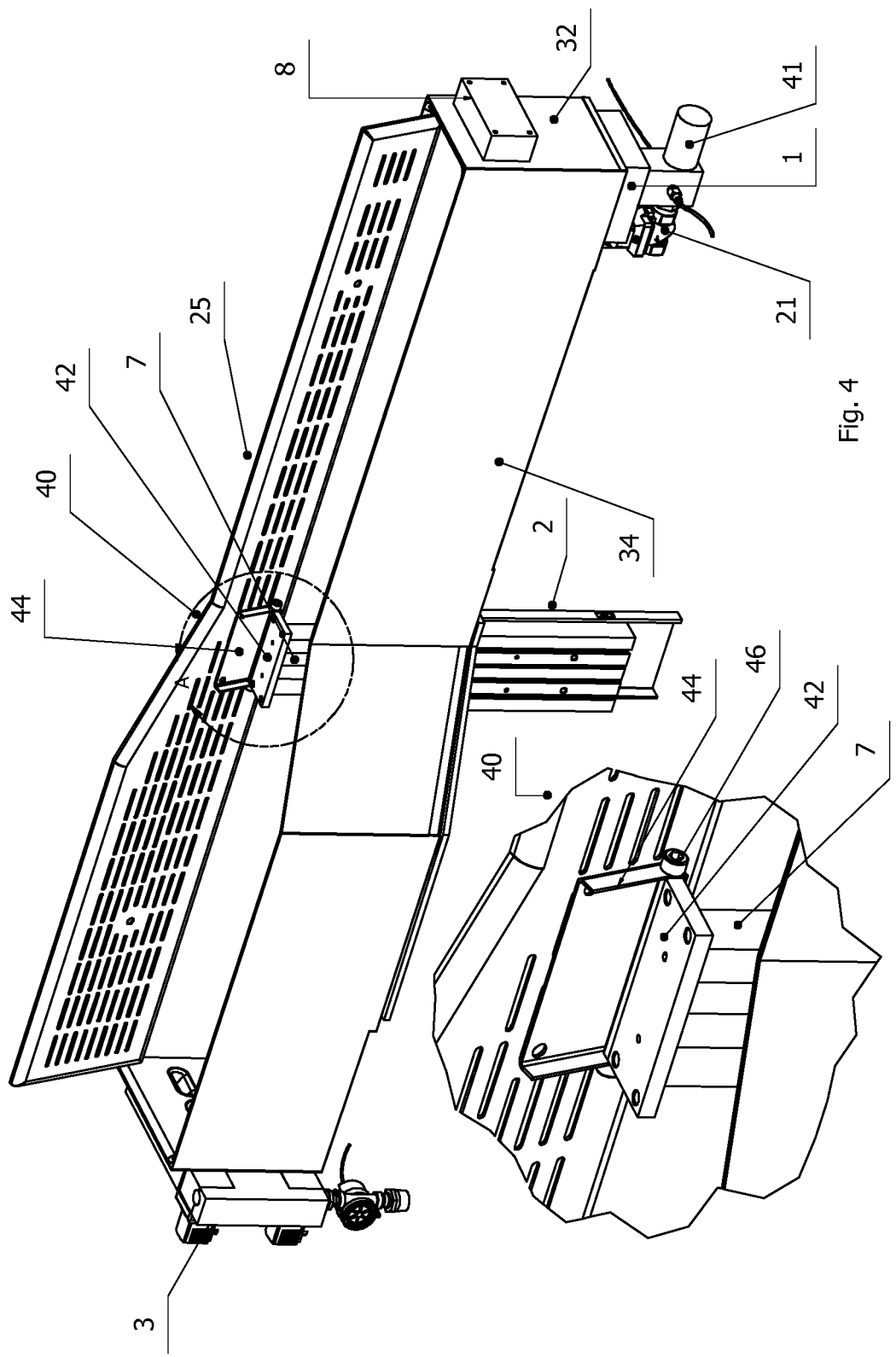

In the sink 10, there is a draining layer 25 provided to support the endoscopes or other medical devices to prevent damage of the endoscopes. The draining layer(s) 25 can be moved up and down by means of a lift system 2 that comprises a plurality, e.g. three actuators. The actuators can be, for example, one or more hydraulic or pneumatic cylinders with one or more pistons 7 that engage with the draining layers 25 to raise and lower them or can be or one or more linear motors or rack and pinion stepper motors. As shown in FIG. 3 and FIG. 4 the lift system 2 can be adapted to lift a draining layer 25 and then rotate the draining layer 25 through and angle so that the layer 25 is inclined to the vertical or is vertical, e.g. through an angle such as 30° to 90°. Preferably the angle through which draining layer 25 rotates provides clear access to the bottom of sink 10 for cleaning. The lift system 2 comprises a plurality of actuators such as three actuators and these can be placed at one spot in the bottom of sink 10 or can be spaced out along the bottom of sink 10 (see FIG. 1). The actuators can be one or more hydraulic or pneumatic pistons 7 or one or more linear motors or rack and pinion stepper motors. The actuators can pass through the bottom of sink 10 and they are then arranged to slide within a liquid tight seal in the bottom of sink 10. As shown in FIG. 3 and FIG. 4 a pusher mechanism 40 can be provided on the top of the lifting system 2 such as on top of pistons 7. The pusher mechanism 40 can include a pusher plate 42 and an angling plate 44. The angling plate 44 may be journaled on pusher plate 42, e.g. by a hinge 46. A driver (not shown) such as a spring may be provided to exert a rotating force on draining layer 25 via angling plate 44. In the retracted position the draining layer 25 can be placed in one or two positions such as a first horizontal lowered position to place an object such as a flexible endoscope or a medical or surgical device optionally having a lumen below the level of the cleaning liquid for a rinsing step. In a second position the lifting system 2 raises the draining layer 25 into a horizontal raised position with the object such as the flexible endoscope or the medical or surgical device optionally having a lumen, above the level of the cleaning liquid to allow manual operation such cleaning e.g. brushing, or drainage, or an inspection. In both these positions the angling plate 44 lies flat on the pusher plate 42. The lifting system 2 can be moved into a third position in which draining layer is raised further to lift and rotate the draining layer 25 so that the layer 25 is at an angle to the vertical, e.g. of 30° to 90° or is vertical. This allows access to the bottom of the sink 10 for cleaning. The angling plate 44 may be fixed to the draining layer 25 e.g. by screws. As indicated above there can be several lifting systems 2 and pusher mechanisms 40 distributed along the bottom of sink 100.

As shown in FIG. 3 and FIG. 4 the draining layer 25 is freely supported by one or more lifting mechanisms. Optionally, movement of the draining layer 25 can be controlled by other means. For example one pin at each end of the draining layer 25 located at a position close to wall 38 can be guided by a vertical slot or track in or on walls 32 and 36 respectively (not shown). As the lifting system 2 moves upwards, the pins slide in the vertical slots until the pins reach the end of the slots. As the lifting system raises the draining layer further, this layer will rotate about the pins. As the lifting system is lowered the draining layer 25 will rotate back to horizontal and the pins will slide vertically down along the slots. With such a lifting system the draining layer 25 can be placed in one or two or three positions such as a first horizontal lowered position to place an object such as a flexible endoscope or a medical or surgical device optionally having a lumen below the level of the cleaning liquid for a rinsing step. In a second position the lifting system 2 raises the draining layer 25 into a horizontal raised position with the pins at the end of the slot or track and with the object such as the flexible endoscope or the medical or surgical device optionally having a lumen, above the level of the cleaning liquid to allow manual operation such cleaning e.g. brushing, or drainage, or an inspection. In both these positions the angling plate 44 lies flat on the pusher plate 42. The lifting system 2 can be moved into a third position in which draining layer is raised further to lift and rotate the draining layer 25 around the axis formed by the pins at the send of the slots or tracks, so that the layer 25 is at an angle to the vertical, e.g. of 30° to 90° or is vertical.

The raising and rotation of layer 25 can be made part of a protocol. For example after a certain time of use the lifting system 2 will operate automatically to raise and rotate layer 25 so that the layer 25 is in an inclined position relative to the vertical or is in a vertical position which prevents further use of the sink 10. For example, the lifting system 2 only lowers the layer 25 after certain cleaning operations have been recorded.

With an automatic lift system 2, after optionally or preferably passing a dry leak test, the porous draining layer 25 supporting the medical devices such as endoscopes can be moved downwards deeper into the sink 10 and into and below the cleaning liquid layer in the sink 10 to rinse the channels of the medical device such as an endoscope. After a suitable length of time in this rinsing step the draining layer 25 will be moved upwards by the lift system 2 to allow brushing of the channels of the medical device such as an endoscope or to allow the endoscope to dry and to be inspected and photographed by camera 3. The camera 3 then starts recording images such as pictures or a movie. These actions can be carried out automatically under the control of the controller.

Subsequently, the draining layer 25 can be moved down to rinse the channels of the medical device such as an endoscope once again. This procedure can be repeated as often as required in accordance for example with a protocol programmed into the controller.

Various supports or other devices to accommodate or to holding objects to be cleaned such as hooks, racks, baskets, trays or caddies can be provided and are not considered to be a limitation on the present invention. It is preferred if the racks, baskets, trays and caddies are used to hold medical or surgical devices even if these devices are small in size and hence to avoid the need for a filter to prevent small devices to leave through the one or more further drains. In other words, any openings in the racks, baskets, trays and caddies should be dimensioned to hold back any expected medical and surgical devices. Optionally, but less preferred, catch elements of a filter can be provided which are shaped and located to hold back small medical and surgical devices or other small objects to remove such objects before the liquid drains out through the one or more drains.

A measurement system is preferably provided to measure any or some or all of:
a) The amount to be dispensed if any additives are to be added to the cleaning liquid. Additives can be provided from any suitable source and dosed via dosing pumps.
b) Level of the liquid in the sink.
c) Temperature of the liquid in the sink.
d) Any restrictions on liquid flow in the cleaning liquid transfer system which are indicative of blockages, e.g. by the provision of one or more sensors, such as pressure and/or flow sensors.
e) Generally, compliance recording equipment to document the cleaning process for each identified medical device such as an endoscope.
f) Any, some or all of these may be logged automatically to demonstrate that the cleaning process was carried out correctly.

The sink preferably has integrated indictor strips 6 such as coloured LED strips to give extra control to the operator during the procedure and to indicate the status of the cleaning process.

In another embodiment a console cleaning system is provided that integrates one or more cleaning sinks as described above with reference to FIGS. 1 to 4. In accordance with another aspect of the present invention such a system is automated through the use of a PLC.

The cleaning sink may be located in suitable furniture such as a table with connections for electrical power, liquid, steam, air pressure and chemical supply.

The invention claimed is:

1. An apparatus for cleaning or pre-cleaning of medical or surgical devices having a lumen, the apparatus comprising:
a sink for holding cleaning liquid, the sink having at least a first wall, a top opening, and a bottom and being adapted to expose objects to the cleaning liquid;
an overflow for draining cleaning liquid that reaches the overflow;
a drain located in the bottom of the sink for draining cleaning liquid from the sink;
a movable draining layer in the sink, movable within the sink in a vertical direction by a lifting system, wherein the lifting system is configured to lift the draining layer from a first horizontal position in cleaning liquid where a rinsing step is able to be performed to a second horizontal position above cleaning liquid, wherein the second horizontal position is below the top opening such that an inspection and manual brushing step can be performed on the medical or surgical devices while the draining layer is in the second horizontal position, and wherein the lifting system is configured to lower the draining layer into cleaning liquid,
further comprising a flushing connection for connecting to a lumen of the medical or surgical devices, wherein the flushing connection is configured to deliver at least one of cleaning liquid, air, or steam into the lumen,
further comprising a compliance recording equipment including an image capture device configured for capturing images of the medical or surgical devices during the brushing step while the draining layer is in said second horizontal position,
wherein the lifting system comprises one or more actuators positioned at the bottom of the sink and is configured to move the draining layer vertically upwards through the sink between the first horizontal position and the second horizontal position.

2. The apparatus according to claim 1, comprising an inlet for injecting cleaning liquid through the first wall.

3. The apparatus according to claim 1, wherein the flushing connection comprises an adapter for connecting to a lumen of the medical or surgical devices.

4. The apparatus according to claim 1, further comprising a bottom skimmer having a plurality of nozzles located in the first wall and configured for inserting liquid through the first wall for moving sunken debris or detritus along the bottom of the tank towards and down the drain, and wherein the bottom skimmer is located at a lower level than an inlet for injecting cleaning liquid.

5. The apparatus according to claim 1, wherein the apparatus is adapted for automatic or manual imaging or video recording, wherein the compliance recording equipment is configured for identification of sink used, wherein the compliance recording equipment is configured for identification of the medical or surgical devices cleaned, and wherein the compliance recording equipment is configured to record operational parameters of the apparatus.

6. The apparatus according to claim 5, wherein the recording of operational parameters of the apparatus include a measured temperature of cleaning liquid and what valves were controlled during a cleaning or pre-cleaning process.

7. The apparatus according to claim 1, further comprising a leakage connection for a leak test of medical or surgical devices to be or being cleaned.

8. The apparatus according to claim 1, wherein the lifting system is adapted to lift the draining layer vertically upwards and then to rotate it through an angle, or
wherein the lifting system is adapted to lift the draining layer vertically upwards and then to rotate it through an angle of between 30° and 90°.

9. The apparatus of claim 8, further comprising a pusher mechanism comprising a driver plate and an angling plate.

10. The apparatus according to claim 1, further comprising a controller for tracing all cleaning steps during the cleaning or pre-cleaning to assure patient and/or endoscope safety and to avoid cross-contamination.

11. The apparatus according to claim 10, further comprising a barcode scanner, a wireless electronic tag detection system, and a recoding system.

12. The apparatus according to claim 1, where the sink does not include a lid.

13. The apparatus according to claim 1, wherein the one or more actuators are configured to pass through the bottom of the sink and are arranged for sliding within a liquid tight seal or wherein the one or more actuators are one or more hydraulic or pneumatic pistons, wherein the one or more actuators are one or more linear motors, or wherein the one or more actuators are one or more rack pinion stepper motors.

14. The apparatus according to claim 1, comprising a controller configured for controlling the image capture device for starting recording images of the manual brushing step when the draining layer is lifted to the second horizontal position.

15. A console cleaning system comprising an apparatus according to claim 1, wherein the console cleaning system comprises a plurality of sinks, and wherein each sink comprises a drain at a lowest point of the respective sink and wherein each sink comprises one or more rows of nozzles for delivery of cleaning liquid into the respective sink.

16. A method of pre-cleaning or cleaning medical or surgical devices having a lumen, in an apparatus for cleaning or pre-cleaning, wherein the apparatus comprises a sink holding cleaning liquid, the sink having at least a wall, a top opening, and a bottom, and wherein the apparatus comprises an overflow for draining cleaning liquid that reaches the overflow, a drain located in the bottom of the sink for draining cleaning liquid from the sink, a movable draining layer in the sink, wherein the draining layer is moveable within the sink in a vertical direction by a lifting system, wherein the lifting system comprises one or more actuators positioned at the bottom of the sink and is configured to lift the draining layer from a first horizontal position in cleaning liquid where a rinsing step is able to be performed to a second horizontal position above an upper level of cleaning liquid, wherein the second horizontal position is below the top opening such that an inspection and manual brushing step can be performed on the medical or surgical devices while the draining layer is in the second horizontal position, and wherein the lifting system is configured to lower the draining layer into cleaning liquid, and wherein the apparatus comprises compliance recording equipment including an image capture device for capturing images of the medical or surgical devices; the method comprising:

performing a leak test on at least one of the medical or surgical devices, lifting the draining layer out of cleaning liquid below the top opening using the lifting system to move the draining layer vertically upwards through the sink between the first horizontal position to the second horizontal position above an upper level of cleaning liquid for an inspection and for a brushing step, performing the brushing step of the medical or surgical devices while the draining layer is below the top opening and in the second horizontal position, capturing images of the medical or surgical devices with the compliance recording equipment during the brushing step while the draining layer is in said second horizontal position, lowering the medical or surgical devices using the draining layer into cleaning liquid for a rinsing step in the first horizontal position, and removing sunken detritus or debris by a directing of cleaning liquid to flow along the bottom of the sink and by draining the sunken detritus or debris and cleaning liquid from the sink.

17. The method of claim 16, further comprising removing floating detritus, bioburden or debris by a directing of cleaning liquid to spill through an overflow.

18. The method of claim 16, further comprising a step of delivering at least one of cleaning liquid, air and steam for the cleaning of objects having a lumen through an outlet.

19. The method of claim 18, further comprising a flushing step for flushing the medical or surgical devices.

20. The method of claim 16, further comprising the step of lifting the draining layer vertically upwards and then rotating it through an angle, or lifting the draining layer vertically upwards and then rotating it through an angle of between 30° and 90°.

* * * * *